(12) United States Patent
Kitagaki et al.

(10) Patent No.: US 6,746,684 B2
(45) Date of Patent: Jun. 8, 2004

(54) MICROENCAPSULATED SOLID PESTICIDES

(75) Inventors: Kenichi Kitagaki, Hyogo (JP); Hironori Kataoka, Nara (JP)

(73) Assignee: Syngenta Crop Protection, Inc., Greensboro, NC (US)

( * ) Notice: Subject to any disclaimer, the term of this patent is extended or adjusted under 35 U.S.C. 154(b) by 6 days.

(21) Appl. No.: 09/977,605

(22) Filed: Oct. 15, 2001

(65) Prior Publication Data

US 2002/0081337 A1 Jun. 27, 2002

Related U.S. Application Data

(63) Continuation of application No. PCT/EP00/03317, filed on Apr. 14, 2000.

(30) Foreign Application Priority Data

Apr. 15, 1999 (JP) .......................................... 11-108445

(51) Int. Cl.$^7$ ............................................... A01N 25/28
(52) U.S. Cl. ...................... 424/419; 424/405; 424/408; 424/417; 427/213.34; 428/407; 514/229.2; 514/361
(58) Field of Search .......................... 504/323; 424/408, 424/417, 419; 427/213.3, 213.34; 428/402.24, 403, 407; 514/229.2, 361

(56) References Cited

U.S. PATENT DOCUMENTS 5,674,519 A * 10/1997 Curtis et al. ................ 424/408

FOREIGN PATENT DOCUMENTS

| WO | WO 91 04661 A | 4/1991 |
| WO | WO 94 22303 A | 10/1994 |

* cited by examiner

*Primary Examiner*—Neil S. Levy
(74) *Attorney, Agent, or Firm*—Rose M. Allen

(57) ABSTRACT

A microcapsule characterized by comprising a solid pesticide as a core material coated with a wall material which is a resin formed by polycondensation of a sparingly water-soluble melamine-formaldehyde resin type prepolymer (said sparingly water-soluble melamine-formaldehyde resin type prepolymer dissolves 2000 g or less of water therein per 100 g of solid component of the prepolymer at +25° C.) in the presence of a dispersant which is a condensation product of naphthalenesulfonic acid and/or alkylnaphthalenesulfonic acid and formaldehyde or a salt thereof, a method for producing said microcapsule, and a method for applying said microcapsule are disclosed.

24 Claims, No Drawings

MICROENCAPSULATED SOLID PESTICIDES

"This application is a continuation of International Application No. PCT/EP00/03317, filed Apr. 14, 2000, the contents of which are incorporated herein by reference."

The present invention relates to a technique for forming a microcapsule of a pesticide, and more particularly to a microcapsule containing a solid pesticide as a core material, which microcapsule is excellent in release-controllability of the pesticidal component, safety, workability, etc.; a composition containing said microcapsule; a method for producing said microcapsule; and a method for application of said microcapsule.

With the aim of controlling the elution of pesticidal component to thereby enhance the durability of pesticidal efficacy and to improve the water-resistance, weather resistance and safety of the pesticide, a variety of microencapsulated pesticides have so far been proposed.

According to such known micro-encapsulation techniques, some of the microcapsules contain a liquid pesticide as a core material. Regarding such liquid core type microcapsules, a technique for forming pesticide droplets by a method of emulsification and coating the droplets with a wall material having a desired thickness has already been developed and practically used without difficulty. On the other hand, regarding solid pesticides including powdery and granular ones, there has so far been provided no microcapsule of satisfactory characteristics because it is quite difficult to make the particle size and shape of such solid pesticides even and to smoothen and uniform the surface thereof. Nevertheless, many of the practically used pesticides are solid materials, and especially in recent years a variety of solid pesticides exhibiting a markedly high efficacy at a very low dose are being manufactured and marketed.

Under these circumstances, Japanese Patent Publication JP-B-2-29642 and Japanese Patent Kokai JP-A-59-6813 have disclosed microcapsules of hydrophobic pesticides using, as the film material, a resin prepared by polycondensation of an amino resin prepolymer with a water-soluble cationic urea resin in the presence of an anionic surfactant, for example. These micro-encapsulated pesticides according to the prior art, however, allow the component contained therein to be eluted out of the capsule in such a short period of time as about 10–20 days. Especially in cases where a powerful solid pesticides such as those mentioned above are contained therein, such rapid release can cause a strong chemical injury, and the released component can cause an significant damage and loss to a cultured crop if such a type of microcapsule is applied to sensitive infant plants just after seeding. Further, for manufacturing a microcapsule of desired type according to the above mentioned prior art microcapsules, it has been necessary to use a hydrophobic solvent exercising an undesirable influence upon the workers, which can be disadvantageous from the viewpoint of safety and cost of manufacture.

In WO 91/04661 an invention is disclosed concerning a microcapsule prepared by adding a liquid-miscible urea, thiourea, melamine-formaldehyde prepolymer or a combination thereof to a suspension of a solid pesticide having a high leachability and curing the mixture. Although this microcapsule was devised for the purpose of weed control, suppression of the leaching of pesticidal component into the areas other than the intended area, namely improving the residence protery in soil and preventing the chemical injury, in the practice this capsule type is insufficient in release-controllability, especially in the relatively early stage after application.

Pesticides according to present invention include fungicides (including plant activators improving the resistance), insecticides, herbicides, plant growth regulators, and the like. These agents, however, are different from one another in the time at which the efficacy of agent is to be exhibited. For instance, in the cultivation of rice plant, an improved harvest can be realized by applying a relatively mild fungicide capable of preventing the injuries caused by viruses and microorganisms to the seedling boxes in which seeding, germination and rooting of the plants are practiced, and then applying an insecticide to repulse the attack of pests in the greening period when spindly growth of stems and leaves occur, if necessary, and then again applying an insecticide and a fungicide just before transplantation to the main paddy field, and after the transplantation by using a herbicide in combination therewith. Especially on big farms cultivating large areas of land, it is desirable to complete the application of pesticides efficiently, i.e. with the smallest frequency of application to the smallest area and preferably with a single application process at the time of seeding and irrigation in the seedling box or in the greening period or just after transplantation, instead of applying the necessary pesticide every time when it is required, because thereby some of the work for cultivation and raising can be saved. If this can be realized, it will lessen the labor necessary for applying pesticides to the large main paddy field after the transplantation, which is quite advantageous.

Even if a powerful solid pesticide is applied in the early stage of plant growth, the occurrence of chemical injury in the infant period of plant can be prevented so far as the solid pesticide is encapsulated in a microcapsule capable of sufficiently controlling the release of component thereof. By such means, the useless loss of active ingredient before the time at which its efficacy is desired can be prevented. Further, the use of such microcapsules will have the beneficial effect of preventing the decomposition of a combination of diverse pesticidally active ingredients in cases where a plurality of pesticidal active ingredients have to be applied in combination at the same time. In the practice often such combinations decompose caused by interaction of the pesticides. The use of microcapsules for at least one component of such combination can prevent the decomposition where otherwise the different pesticides cannot be used in one single conventional formulation and must then be applied separately.

In view of the above, the object of the present invention consists in providing a microcapsule containing a solid pesticide which has a desirable ability to control the leaching of the active component thereof and can realize an improved workability with a suppressed occurrence of chemical injury.

In order to achieve the above-mentioned objective, the present invention provides a microcapsule with the desirable characteristic properties, even when the core material is a solid pesticide. The microcapsules according to the invention may be obtained by subjecting a prescribed melamine-formaldehyde resin type prepolymer showing a sparingly water-soluble property to a polycondensation reaction in the presence of a dispersant which is a condensation product of naphthalenesulfonic acid and/or alkylnaphthalenesulfonic acid and formaldehyde or a salt thereof.

Accordingly, the first aspect of the present invention is a microcapsule characterized by coating a solid pesticide as a core material with a wall material which is a resin formed by subjecting a sparingly water-soluble melamine-formaldehyde resin type prepolymer to a polycondensation reaction in the presence of a dispersant which is a condensation product of a naphthalenesulfonic acid and/or alkylnaphthalenesulfonic acid and formaldehyde or a salt thereof, provided that the solubility of water in said sparingly water-soluble melamine-formaldehyde resin type prepolymer is 2000 g or less at +25° C. per 100 g of solid component of said prepolymer.

Said dispersant is preferably sodium naphthalenesulfonate-formaldehyde condensation product having a weight-average molecular weight of 500 to 8000 (the second aspect of the present invention). By using such a dispersant, both the solid pesticide constituting the core material and the microcapsule formed by polycondensation of the prepolymer can be mono-dispersed in a desirable state in the reaction mixture without agglomeration of the sparingly water-soluble melamine-formaldehyde resin type prepolymer.

As said solid pesticide used as the core material, those having a melting point of +20° C. or above are preferably used (the third aspect of the present invention).

The above-mentioned microcapsule is successfully usable for raising rice plants (the fourth aspect of the present invention). Since this microcapsule has a desirable slow-release property, the microencapsulated pesticidal component can be applied without the risk of any adverse influence even in the growing period and especially in the infant period of rice plant in which the rice plant is most susceptible to chemical injury of pesticides, i.e. the period of from just after seeding to shortly before transplantation.

As the core material of the microcapsule of the present invention, Acibenzolar-S-methyl which is a solid pesticide having a melting point of +20° C. or above is suitably used (the fifth aspect of the present invention). A microcapsule using such a solid pesticide is preferable for application to rice plants because of the favourable slow-releasing property thereof.

The sixth aspect of the present invention is a method for producing a microcapsule. The method is characterized by comprising a step of dissolving in water a dispersant which is a condensation product of a naphthalenesulfonic acid and/or alkylnaphthalenesulfonic acid and formaldehyde or a salt thereof, a step of adding a sparingly water-soluble melamine-formaldehyde resin type prepolymer to the solution obtained above while stirring the solution, a step of adding a solid pesticide thereto and carrying out polycondensation of said prepolymer under an acidic condition, provided that the solubility of water in said sparingly water-soluble melamine-formaldehyde resin type prepolymer is 2000 g or less at +25° C. per 100 g of solid component of the prepolymer. By such a method of production, the intended microcapsule can be provided.

In the method mentioned above, it is preferable to use the solid pesticide in an amount of 1–50% by weight, the dispersant in an amount of 1–20% by weight and the sparingly water-soluble melamine-formaldehyde resin type prepolymer in an amount of 1–60% by weight, based on the liquid mixture subject to the polycondensation reaction (the seventh aspect of the present invention). By using such a liquid reaction mixture, the individual solid pesticide particles can be mono-dispersed and the prepolymer can be polycondensated so as to coat each particle with the resin uniformly.

As said dispersant, a sodium naphthalenesulfonate-formaldehyde condensation product having a weight average molecular weight of 500 to 8000 is preferably used (the eighth aspect of the present invention) and, as said solid pesticide, those having a melting point of +20° C. or above are preferably used (the ninth aspect of the present invention). Then, according to the above-mentioned method of production, there can be produced a microcapsule endowed with desired characteristic properties for use in raising rice plants (the tenth aspect of the present invention). It has been revealed that, as the solid pesticide used in such a method of production, Acibenzolar-S-methyl which is a solid pesticide having a melting point of +20° C. or above is especially preferred (the eleventh aspect of the present invention).

Further, the twelfth aspect of the present invention aims at a microcapsule characterized by having been produced according to the method for production according to the above-mentioned sixth to eleventh aspects of the present invention.

Further, it is preferred that the above-mentioned microcapsule starts the release of pesticidal component upon contact with water the weight of which is 100 times or above as much as the weight of the microcapsule (the thirteenth aspect of the present invention). So far as the releasing characteristic is controlled so as to be exhibited depending on the environmental condition (rate of dilution with water), there can be obtained a good result. Thus, even if an aqueous suspension containing the microcapsule at a high concentration or if the solid microcapsule itself is applied in the raising of rice plant in the period of from the seeding to the transplantation, the pesticidal component is not released from the microcapsule in the seedling box and therefore it causes no chemical injury there, and the pesticidal component is firstly released from the microcapsule to exhibit its efficacy after the greened rice plant is transplanted into the main paddy field or into an environment rich in water.

The fourteenth aspect of the present invention is an aqueous suspension containing the above-mentioned microcapsule in an amount of 2% by weight or more. After the preparation by the method of polycondensation, the above-mentioned microcapsule is subject to a proper treatment and can be distributed in the form of liquid or solid composition. From the standpoint of workability, an aqueous suspension composition is preferred.

The fifteenth aspect of the present invention aims at a method for applying a microcapsule characterized by scattering the above-mentioned microcapsule to a soil on which plants grow up. The sixteenth aspect of the present invention is a method characterized by applying a microcapsule to the soil on which plants grow up at the time of sowing plants seeds or in the growing period of plants. Since the release of solid pesticidal component from microcapsule can be sufficiently controlled according to the present invention, the intended efficacy can be exhibited in the desired period of time without any serious chemical injury even if the microcapsule is applied in the infant period of the plants.

The seventeenth aspect of the present invention is a method characterized by scattering the above-mentioned microcapsule to the soil on which plants grow up in the period between the time of sowing rice seeds and the time of transplanting rice seedling to the main paddy field. According to this method, the labor necessary for applying a pesticide to a large paddy field can be saved and the desired efficacy can be exhibited in the proper period while suppressing the occurrence of chemical injury. If desired, the microcapsule may be directly applied to the main paddy field after transplanting the rice seedling to the main paddy field (the eighteenth aspect of the present invention).

In the present invention, the sparingly water-soluble melamine-formaldehyde resin type prepolymer is a material for forming the coating film of microcapsule, i.e. the material for forming the wall. It is a preliminary condensation product of the resin obtained by polymerization of melamine and formaldehyde. As used in the present invention, the term "preliminary condensate" means a condensation product which is not yet completely converted to a resin and shows a liquid state at ordinary temperature.

The melamine-formaldehyde resin type prepolymer is prepared, for example, in the following manner. That is, (a) melamine powder and (b) formalin (37% by weight aqueous solution of formaldehyde) are mixed together at a molar ratio (a:b) of 1:1.5 to 1:6.0, and the mixture is heated at about +60° C. or above under a weakly alkaline condition. In this manner, melamine-formaldehyde resin prepolymers the properties of which vary in a wide range, from sparingly water-soluble to water-soluble can be obtained. In the prepolymer, a higher value of (a), namely a higher proportion of melamine powder, gives a lower permeability and a higher slow-releasing property to the ultimately obtained coating film.

It is also acceptable to prepare and use a modified melamine-formaldehyde resin prepolymer in the present invention. The modified melamine-formaldehyde resin prepolymer can be prepared by alkylating the melamine-formaldehyde resin prepolymer obtained above with an alkyl alcohol such as methyl alcohol, ethyl alcohol, isopropyl alcohol, butyl alcohol or the like in the presence of a very small quantity of acidic substance or by crosslinking the melamine-formaldehyde resin prepolymer with a glycol such as ethylene glycol, propylene glycol or the like. The glycol-modified prepolymers are especially preferred because the solubility of water therein can easily be controlled to a desired value.

As the melamine-formaldehyde resin type prepolymer, a variety of ones can be prepared by varying the molar ratio of melamine to formaldehyde or by adopting the method of alcohol modification as mentioned above. Including the modified products, the melamine-formaldehyde resin type prepolymers used in the present invention show a sparingly water-soluble nature. As used herein, the term "sparingly water-soluble nature" means a low solubility of water in the prepolymer itself. More concretely saying, the present invention uses a melamine-formaldehyde resin type prepolymer in which 2000 g or less of water can be dissolved at +25° C. per 100 g (weight of solid component) of the melamine-formaldehyde resin type prepolymer. This means that such a prepolymer forms a precipitate in water when the quantity of water exceeds 2000 g. Preferably, the quantity of water having a temperature of +25° C. to be taken up into 100 g of the melamine-formaldehyde resin type prepolymer is 100 to 1400 g. If the quantity of water capable of being dissolved in 100 g of the prepolymer exceeds 2000 g, such a prepolymer has an excessively high water-solubility, so that, after formation of microcapsule, the wall material can not retain the intended slow-releasing effect of the core material. As a preferable example of such a sparingly water-soluble melamine-formaldehyde resin type prepolymer suitably usable in the present invention, a glycol-modified melamine-formaldehyde resin prepolymer manufactured by Miki Riken Kogyo K. K. and marketed under the trade name of Rikensol® PHW-35, which can dissolve 1000–1400 g of water therein at +25° C. per 100 g of prepolymer (weight of the solid component), can be referred to. The prepolymer referred to above is usually put to use in the form of an aqueous solution having a concentration of 50 to 80% by weight.

The dispersant used in the present invention is a condensation product formed from naphthalenesulfonic acid and/or alkylnaphthalenesulfonic acid and formaldehyde or a salt thereof. If a polyoxyalkylene monoether type surfactant or a salt of alkylphenylsulfonic acid type surfactant and the like which are commonly used as known dispersant or emulsifier are used as the dispersant for the polymerization of the prepolymer of the invention, then a self-agglomeration of prepolymer takes place, which makes the water-solubility too low.

In such condensates formed from naphthalenesulfonic acid and/or alkylnaphthalenesulfonic acid and formaldehyde or a salt thereof, molar ratio of the naphthalenesulfonic acid and/or alkylnaphthalenesulfonic acid to formaldehyde is appropriately selected so as to agree with the preferable molecular weight range.

The condensation product is prepared by firstly sulfonating naphthalene, an alkylnaphthalene (the number of alkyl groups is preferably 1 or 2 and the position of substitution is not critical) such as methylnaphthalene, ethylnaphthalene, butylnaphthalene, dimethylnaphthalene and the like or a mixture thereof with sulfuric acid, adding thereto water and formalin and then carrying out a condensation reaction under an acidic condition. Then, if necessary, a salt may be formed therefrom by the use of an alkaline metal ion, alkaline earth metal ion, ammonia or an amine. Of these salts, salts of alkaline metals such as sodium, potassium and the like and salts of alkaline earth metals such as calcium, magnesium and the like are preferred, and sodium salt is especially preferred. The dispersants preferably used in the present invention are sodium naphthalenesulfonate-formaldehyde condensation product, and those having a weight-average molecular weight of 500 to 8000 as measured by gel permeation chromatography (GPC) are especially preferred. An example thereof is Labellin® FH-L (trade name) manufactured by Dai-ichi Kogyo Seiyaku Co., Ltd. By using such a dispersant, dispersibility of the microcapsule formed by the polycondensation and the core material are both improved, and a desired microcapsule can be produced. As used herein, the conditions of GPC are as follows:

Column: TSK-GEL G-3000SW, G-4000SW and pre-column, manufactured by Toyo Soda Co. Ltd.
Eluent: Acetonitrile/0.05M aqueous solution of sodium acetate=40/60 by volume, pH 6.88
Flow rate: 0.85 ml/minute
Wavelength of detection: 254 nm
Standard substance: Sodium polystyrenesulfonate The solid pesticide constituting the core material in the present invention is a pesticidal component having a solid state at ambient temperature, such as powder, granule and the like. A melting point of +20° C. or above is sufficient for the purpose of the invention. Particle diameter of the solid pesticide just before encapsulation is preferably 0.5 to 90 μm, and especially 0.5 to 60 μm. If the solid pesticide is a fine particle having a too small particle diameter the surface area to be covered with the wall amterial becomes too large. On the other hand, if the particle diameter is too large, the microcapsule obtained therefrom tends to cause problems such as clogging at the time of application of its aqueous suspensions using a water-irrigating means such as watering pot or spraying device.

The solid pesticides which can be used in the present invention in the above-mentioned manner include solid herbicides, solid fungicides and solid insecticides for paddy field rice plants.

As solid herbicides for paddy field rice plants, there are for example
(R,S)2-(2,4-dichloro-3-methylphenoxy)propionanilide (Clomeprop; solubility in water: 0.032 ppm at +25° C.), methyl-5-(2,4-dichlorophenoxy)-2-nitrobenzoate (Bifenox; solubility: 0.35 ppm),
2-[4-(2,4-dichlorobenzoyl)-1,3-dimethylpyrazol-5-yl-oxy] acetophenone (Pyrazoxyfen; solubility: 0.9 ppm at +20° C.),
4-(2,4-dichlorobenzoyl)-1,3-dimethylpyrazol-5-yl-toluene-4-sulfonate (Pyrazolate; solubility: 0.056 ppm at +25° C.),
S-1-methyl-1-phenylethylpiperidine-1-carbothiolate (Dimepiperate; solubility: 20 ppm),
3-(4,6-dimethoxypyrimidin-2-yl)-1-[(2-methoxycarbonylbenzyl)sulfonyl]urea (Bensulfuron-methyl; solubility: 2.9 ppm at pH 5, +25° C.),
4-(2,4-dichlorobenzoyl)-1,3-dimethylpyrazol-5-yl-toluene-4-sulfonate (Pyrazosulfuron-ethyl; solubility: 14.5 ppm at +20° C.),
2-(2-naphthyloxy)propionanilide (Naproanilide; solubility: 0.74 ppm at +27° C.),
2-bromo-3,3-dimethyl-N-(1-methyl-1-phenylethyl) butyramide (Bromobutide; solubility: 3.54 ppm at +25° C.),
2-benzothiazol-2-yloxy-N-methylacetoanilide (Mefenacet; solubility: 4 ppm),
N-(2-chloroimidazole[1,2-a]pyridin-3-ylsulfonyl)-N'-(4,5-dimethoxy-2-pyrimidyl)urea (Imazosulfuron; solubility: 67 ppm at pH 6),
1-(α,α-dimethylbenzyl)-3-(p-tolyl)urea (Dymron; solubility: 1.7 ppm at +20° C.),
3-isopropyl-2,1,3-benzothiadiazinone-(4)-2,2-dioxide (Bentazone; solubility: 500 ppm at +20° C.),
2,4-bis(ethylamino)-6-methylthio-1,3,5-triazine (Simetryne; solubility: 450 ppm),
2',3'-dichloro-4-ethoxymethoxybenzanilide (Etobenzanide; solubility: 1.2 ppm at +20° C.),
butyl(R)-2-[4,4-(cyano-2-fluorophenoxy)phenoxy] propionate (Cyhalofop-butyl; solubility: 0.7 ppm at pH 7, +20° C.),
1-(diethylcarbamoyl)-3-(2,4,6-trimethyl)phenylsulfonyl-1,2,4-triazole (Cafenstrole; solubility: 2.5 ppm at +20° C.),
3-(4,6-dimethoxypyrimidin-2-yl)-1-[(1-methyl-4-(2-methyl-2H-tetrazol-5-yl)pyrazol-5-yl-sulfonyl)urea (Azimsulfuron; solubility: 72.3 ppm at pH 5),
methyl-2-[(4,6-dimethoxypyrimidin-2-yl)oxy]-6-[1-(methoxyimino)ethyl]benzoate (Pyriminobac-methyl; solubility: 1 ppm at +20.4° C.),
2-[4-(2,4-dichloro-m-toluoyl)-1,3-dimethylpyrazol-5-yloxy]-4'-methylacetophenone (Benzofenap; solubility: 0.11 ppm at +20° C.),
O-3-tert-butylphenyl-N-(6-methoxy-3-pyridyl)-N-methyl (thiocarbamate) (Pyributycarb; solubility: 0.32 ppm),
2-chloro-N-(3-methoxy-2-thienyl)methyl-1,2',6'-dimethylacetanilide (Thenylchlor; solubility: 11 ppm],
4-(4-chloro-o-toluyloxy)butyric acid (MCPB; solubility: 44 ppm),
3-(4,6-dimethoxy-1,3,5-triazin-2-yl)-1-[2-(2-methoxyethoxy)phenylsulfonyl]urea (Cinosulfuron; solubility: 82 ppm at pH 5, +20° C.).

As solid fungicides for paddy field rice plants, there are for example benzo[1,2,3]thiadiazole-7-carbothioic acid S-methyl ester (Acibenzolar-S-methyl; solubility: 7.7 ppm at +25° C.),
diisopropyl-1,3-dithiolan-2-ylidene-malonate (Isoprothiolane; solubility: 50 ppm),
(1RS, 2SR, 5RS)(1RS, 2SR, 5SR)-2-(4-chlorobenzyl)-5-isopropyl-1-(1H-1,2,4-triazol-1-ylmethyl)cyclopentanol (Ipconazole; 6.74 ppm),
3-(3,5-dichlorophenyl)-N-isopropyl-2,4-dioxoimidazolidine-1-carboxyamide (Iprodione; solubility: 13 ppm),
5-ethyl-5,8-dihydro-8-oxo[1,3]dioxolo[4,5-g]quinoline-7-carboxylic acid (Oxolinic acid; solubility: 3.2 ppm),
Kasugamycin hydrochloride (Kasugamycin; solubility: 125000 ppm),
2,2-dichloro-N-[1-(4-chlorophenyl)ethyl]-1-ethyl-3-methylcyclopropanecarboxamide (Carpropamide, 1.7 mg/lwater at pH 7 and +20° C.),
N-trichloromethylthiotetrahydrophthalimide (Captan; solubility: 3.3 ppm),
2-(4-thiazolyl)benzimidazole (Thiabendazole; solubility: 10000 ppm at pH 2.0, 25° C.; less than 50 ppm at pH 5–12),
bis(dimethylthiocarbamoyl)disulfide (Thiram; solubility: 30 ppm),
1,2-bis(3-methoxycarbonyl-2-thioureido)benzene (Thiofanate-methyl; solubility: sparingly soluble),
bis(quinolin-8-olato-O,N)copper (Oxine-copper; insoluble),
5-methyl-1,2,4-triazolo[3,4-b]benzothiazole (Tricyclazole; solubility: 700 ppm),
(E)-4-chloro-α,α,α-trifluoro-N-(1-imidazol-1-yl-2-propoxyethylidene)-o-toluidine (Triflumizole; 12.5 ppm at pH 5.9),
Validamycin A (Validamycin; solubility: readily soluble),
3-hydroxy-5-methylisoxazole (Hydroxyisoxazole; solubility: 90000 ppm),
methyl (E)-2-{2-[6-(2-cyanophenoxy)pyrimidin-4-yloxy] phenyl}-3-methoxyacrylate (Azoxystrobin, 6 mg/l water at +20° C.),
1,2,5,6-tetrahydropyrrolo(3,2,1-ij)quinolin-4-one (Pyroquilon; solubility: 4000 ppm),
4-(2,2-difluoro-1,3-benzodioxol-4-yl)pyrrole-3-carbonitrile (Fludioxonil; solubility: 1.8 ppm at +25° C.),
N-propyl-N-[2-(2,4,6-trichlorophenoxy)ethyl]imidazole-1-carboxamide (Prochloraz; solubility: 55 ppm at +25° C.),
3-allyloxy-1,2-benzoisothiazole-1,1-dioxide (Probenazol; solubility: 150 ppm),
methyl-1-(butylcarbamoyl)-2-benzimidazole carbamate (Benomyl; solubility: 4 ppm at pH 3-10),
S-(4-methylsulfonyloxyphenyl)-N-methylthiocarbamate (Metasulfocarb; solubility: 480 ppm),
tetrachloroisophthalonitrile (Chlorothalonil; solubility: 0.6 ppm).

As solid insecticides for paddy field rice plants, there are for example diisopropyl-1,3-dithiolan-2-ylidene-malonate (Isoprothiolane; solubility: 50 ppm),
1-(6-chloro-3-pyridylmethyl)-N-imidazolidin2-ylideneamine (Imidacloprid; solubility: 510 ppm),
2-(4-ethoxyphenyl)-2-methylpropyl-3-phenoxybenzylether (Ethofenprox; solubility: less than 0.001 ppm),
1,3-bis(carbamoylthio)-2-(N,N-dimethyamino)propane hydrochloride (Cartap; solubility: 200000 ppm at +25° C.),
3-(2-chlorothiazol-5-ylmethyl)-5-methyl-[1,3,5] oxadiazinan-4-ylidene-N-nitroamine (Thiamethoxam; solubility: 3265 ppm),
5-dimethylamino-1,2,3-trithiane oxalate (Thiocyclam; solubility: 84000 ppm at +23° C.),
S,S'-2-dimethylaminotrimethylene-di(benzenethiosulfonate) (Bensultap; solubility: 0.7-0.8 ppm),
2,2-dimethyl-1,3-benzodioxol-4-ylmethylcarbamate (Bendiocarb; solubility: 40 ppm at +25° C.),
3-(dimethoxyphosphonyloxy)-N-methyl-cis-crotonamide (Monocrotofos; solubility: 1000000 ppm),
2-isopropoxyphenyl-N-methyl carbamate (Propoxur (PHC); solubility: 2000 ppm).

Needless to say, these examples are not limiting the invention, but serve as illustration of the present invention which can be applied to a variety of other solid pesticides known so far.

Among these pesticides, fungicides such as Acibenzolar-S-methyl (benzo[1,2,3]thiadiazole-7-carbothioic acid S-methyl ester, mp. ca. 133° C.), Fludioxonil (4-(2,2-difluoro-1,3-benzodioxol-4-yl)pyrrole-3-carbonitrile, mp. ca. 200° C.), Pyroquilon (1,2,5,6-tetrahydropyrrolo (3,2,1-ij)quinolin-4-one, mp. ca. 112° C.), and the like, insecticides such as Thiamethoxam (3-(2-chlorothiazole-5-ylmethyl)-5-methyl[1,3,5]oxadiazinan-4-ylidene-N-nitroamine, mp. ca. 139° C.), Thiocyclam (5-dimethylamino-1,2,3-trithianen oxalate, mp. ca. 126° C.), Pymetrozine ((E)-4,5-dihydro-6-methyl-4-(3-pyridimethyleneamino)-1,2,4-triazine-3(2H)-one, mp. ca. 217° C.) and the like, and herbicides such as Cinosulfuron (1-(4,6-dimethoxy-1,3,5-triazin-2-yl)-3-[2-(2-methoxyethoxy)phenylsulfonyl]urea, mp. ca. 141° C.) and the like, all manufactured by Novartis Agro K. K., can successfully be used. Especially, Acibenzolar-S-methyl is preferred as a core material of the microcapsule of the present invention.

For preparing the microcapsule of the present invention from the above-mentioned ingredients, a dispersant selected from naphthalenesulfonate-formaldehyde condensation product, alkylnaphthalenesulfonate-formaldehyde condensation product and combination thereof is dissolved in water, and then a sparingly water-soluble melamine-formaldehyde resin type prepolymer is added to the solution obtained in above while stirring the solution. Subsequently, a solid pesticide is added, the resulting mixture is acidified using a pH regulator, and a polycondensation of the prepolymer is carried out.

Recommendably, the solid pesticide as the core material is used in an amount of 1 to 50% by weight based on the reaction mixture of polycondensation. If the amount of solid pesticide in the microcapsules is rather low, the result is not satisfactory from the viewpoint of economy. If it is amount is too high, no stable microcapsule dispersion can be obtained.

The sparingly water-soluble melamine-formaldehyde resin type prepolymer is added in an amount sufficient for covering the whole surface of the individual particles of the solid pesticide used as a core material. That is, the prepolymer is preferably used in an amount falling in the range of from 1% to 60% by weight based on the reaction mixture of polycondensation. If the amount of the prepolymer is too low, it is difficult to encapsulate individual particles of the solid pesticide. If the amount of the prepolymer is too high, the excessive portion of the prepolymer agglomerates to form resin beads containing no solid pesticide as core material.

Preferably, the dispersant is added in an amount with which both the solid pesticide and the resulting microcapsules can be sufficiently dispersed. For example, it is preferred to preset the amount of the dispersant so as to fall in the range of from 1% to 20% by weight based on the reaction mixture of polycondensation. If the amount of the dispersant is as low as less than 1% by weight, there is a tendency that the system is insufficient in dispersing effect. If the dispersant is added in such a large amount as exceeding 20% by weight, no additional improvement of dispersibility is achieved with a mere increase of the manufacturing cost.

The ingredients mentioned above are compounded by the procedures mentioned above, and the pH value of the system is adjusted to an acidity, preferably in a pH range of from 3 to 7, with a pH regulator such as citric acid, phosphoric acid, boric acid, hydrochloric acid or the like. From the viewpoint of safety to living organisms, citric acid is preferred among the pH regulators. The mixture thus prepared is subject to polycondensation with stirring at a temperature of +10 to +80° C., preferably +50 to +70° C., for 5 to 6 hours, by which a microcapsule of the present invention can be obtained.

Particle diameter of the microcapsule is adjusted to 1 to 100 μm, and preferably 1 to 80 μm. Thickness of the wall material constituting the coating may be arbitrarily selected according to purposes. A too large particle diameter of the microcapsule can cause clogging or the like of the irrigating means at the time of applying the microcapsule, as has been mentioned above. A too small particle diameter of the microcapsule can make the manufacture of microcapsule difficult.

The microcapsule which has been produced in the above-mentioned manner allows to control the releasing characteristic of the active ingredient sufficiently. Thus, according to the invention, it becomes possible to control the releasing characteristic so as to start the release of pesticidal component when the microcapsule is brought into contact with water in a weight ration which is from one hundred to 200 thousand times higher the weight of the microcapsule, which is especially favorable in the culture of rice plant.

The microcapsule which has been obtained as an aqueous dispersion in the above-mentioned manner is recommendably formed into an aqueous suspension composition containing the solid pesticide-including microcapsule in an amount of 2% by weight or more, and preferably 2 to 90% by weight. The composition may comprise multiple kinds of microcapsules produced according to the method of the present invention. Other non-encapsulated active ingredients such as other fungicide and the like, nutrients, stabilizer, and the like may also be added thereto appropriately. Even multiple kinds of pesticides which can not be compounded together in a single conventional formulation, according to the invention can be made to co-exist in one aqueous suspension and distributed in a single application as far as they are separately encapsulated according to the present invention.

If desired, the microcapsule dispersion obtained by the above-mentioned method of the present invention can be made water-free and recovered in the form of a solid. This solid microcapsule may appropriately be mixed into granular compositions, wettable powder compositions, dust compositions or soil for cultivation. The method for separating water from the aqueous dispersion of microcapsule is not particularly limited, but so far known methods such as centrifugation, filtration under elevated pressure, spray drying, and the like can be adopted.

In the following, the method for applying the microcapsule of the present invention is described.

The objects to which the microcapsule of the present invention can be applied involve all the general vegetation, and are not particularly limited. The time of application thereof is also not particularly limited, but the microcapsule of the invention can be applied in the infant period of plants, too. If multiple kinds of microcapsules containing a plurality of solid pesticides are made into one composition and applied at the time of sowing seeds or at the time of irrigation, a highest saving of labor can be realized, which may be quite advantageous.

Application of the microcapsule to rice plants constructs some preferred embodiments of practice of the present invention. The preferred embodiments include (1) treatment at the time of sowing seeds, namely application to the nursery bed soil to be transferred into the seedling box, or application simultaneously with sowing seeds or at the time of irrigation just after seeding, (2) treatment in the greening period, namely application in the greening period after germination which follows after sowing seeds into the seedling box and covering them with soil, (3) treatment just before transplantation, namely application after raising seedlings and just before transplanting the seedlings into the main paddy field, and/or (4) direct application to the main paddy field. Although a microcapsule which has been made into a solid can also be used, the application can easily be achieved by preparing an aqueous suspension composition of microcapsule and applying the suspension to the seedling box by means of seeding machine, spraying machine, irrigating machine or the like.

Next, the present invention is explained with reference to examples. Needless to say, the invention is by no means limited by these examples.

EXAMPLE 1

Formulation
(1) Solid pesticide: 10 g of Acibenzolar-S-methyl (fungicide for paddy field rice plants, manufactured by Novartis Agro K. K.) having a mean particle size of 60 µm
(2) 5 g of a 50% (by weight) aqueous solution of sparingly water-soluble melamine-formaldehyde resin type prepolymer: a glycol-modified melamine-formaldehyde resin prepolymer [Rikensol® PHW-35 (trade name), manufactured by Miki Riken Kogyo K. K., capable of letting 1000–1,400 g of water dissolve in 100 g of solid component thereof at +25° C.]
(3) Dispersant: 10 g of a 50% (by weight) aqueous solution of sodium naphthalenesulfonate-formaldehyde condensation product [Labellin® FH-L (trade name) manufactured by Dai-ichi Kogyo Seiyaku Co., Ltd., weight-average molecular weight 5,240 as measured by GPC]
(4) 1.0 g of a 20% aqueous citric acid solution
(5) 74 g of water Method of Production The sodium naphthalenesulfonate-formaldehyde condensation product (3) was dissolved in water (5) at +50° C. While stirring the resulting aqueous solution at 300 rpm, the glycol-modified melamine-formaldehyde resin type prepolymer (2) was added to the solution, and then the solid pesticide (1) was compounded and emulsified. Subsequently, the emulsion thus obtained was adjusted to pH 4.0 with citric acid (4). By stirring the mixture thus obtained at +50° C. for 5 hours at 300 rpm, the melamine-formaldehyde resin prepolymer was subject to an in situ polycondensation reaction on the surface of the solid pesticide particles which form the core material, and thereby a coating film of the condensation product was formed. Thus, a dispersion of microcapsule including Acibenzolar-S-methyl was obtained.

A measurement using a Laser Diffraction Type Particle Size Distribution Apparatus (SALD-2000, manufactured by Shimadzu Seisakusho) revealed that particle diameter of the microcapsule obtained above was ca. 70 µm.

EXAMPLE 2

A microcapsule dispersion was prepared in the same manner as in Example 1, except that the 20% aqueous citric acid solution was used in an amount of 2.0 g and the total quantity of the composition was adjusted by controlling the amount water. The same measurement as in Example 1 revealed that the microcapsule obtained above had a particle diameter of 90 µm.

COMPARATIVE EXAMPLE 1

A microcapsule was tentatively prepared in the same manner as in Example 1, except that the sodium naphthalenesulfonate-formaldehyde condensation product used as a dispersant was replaced with 5 g of polyoxyethylene lauryl ether. However, a dumpling-like resin mass was formed in the step of emulsification, and no microcapsule could be prepared.

COMPARATIVE EXAMPLE 2

A microcapsule was prepared according to the same formulation and processed as in Example 1, except that the sparingly water-soluble melamine-formaldehyde resin type prepolymer (2) used in Example 1 was replaced with 5 g of water-soluble melamine-formaldehyde resin prepolymer [Rikensol® MA-31 (trade name), manufactured by Miki Riken Kogyo K. K., capable of dissolving at least 2,100 g of water in 100 g of solid component thereof]. The same measurement as in example 1 revealed that particle diameter of the microcapsule thus obtained was 65 µm.

Each of the microcapsules obtained in Examples 1,2 and Comparative Example 2 mentioned above was made into an aqueous suspension containing 10% by weight of microcapsule, and subject to the following tests.

TEST EXAMPLE 1

Elution Test

The microcapsule suspensions prepared in Examples 1 and 2 and Comparative Example 2 were tested to investigate the elution of pesticidal component in water as a function of time. Fifty milligrams of each microcapsule suspension was used in the tests. Further, as a referential example, 250 mg of commercial granular composition of Acibenzolar-S-methyl (BION Granule 2, manufactured by Novartis Agro K. K.) was also tested similarly. This granular composition contained Acibenzolar-S-methyl in an amount of 2%, having been subject to a coating treatment using a polymer. It had already acquired an official registration as a rice seedling box treating agent before transplantation.

First, each sample was introduced into a one liter Erlenmeyer flask with ground stopper containing one liter of deionized water. After allowing the sample to stand at ambient temperature for a prescribed period of time (days), the test fluid was homogenized with stirring. Then, 10 ml of elution test sample fluid were taken out from a position 10 mm apart from the flask wall on a plane equally bisecting the distance from the liquid surface to the bottom. The sample taken out was transferred into a centrifuge tube having a capacity of 50 ml, and filtered with a 0.45 µm membrane filter. Then, thereto was added 2.5 ml of a solution of 0.01 mg of methyl benzoate (prepared by Wako Pure Chemicals K. K.) in acetonitrile as an internal standard substance.

The elution test solution thus obtained was subject to a high performance liquid chromatography to determine the quantity of eluted Acibenzolar-S-methyl. The determination was carried out by injecting 50 µl of the sample solution into a high performance liquid chromatography apparatus (LC-6A, manufactured by Shimadzu Seisakusho) equipped with a Nucleosil 5-Cs column (diameter: 4.6 mm×250 mm) operated at a column temperature of +50° C. and at a flow rate of 1 ml/minute, using a 40/60 mixture (by volume) of acetonitrile/a 0.1% aqueous phosphoric acid solution as an eluent. As a result of the chromatographic analyses, an elution pattern at 254 nm was detected by the ultraviolet detector (SPD-6A, manufactured by Shimadzu Seisakusho). The peak area was measured and enumerated by means of Chromatopak CR4A manufactured by Shimadzu Seisakusho. With reference to a result of similar chromatography using a pure sample of Acibenzolar-S-methyl as a standard, the quantity of Acibenzolar-S-methyl present in each test sample was determined and calibrated by referring to the theoretical value of standard substance, from which elution rate per charged pesticidal component was calculated.

The results are summarized in Table 1. Table 1 demonstrates that in the microcapsules of Examples 1 and 2 the elution rate remained at a low level of 2–3% until the $7^{th}$ day so that the total elution reached only about 14% in two weeks. On the other hand, in the microcapsule of Comparative Example 2, which was prepared from the water-soluble melamine-formaldehyde resin type prepolymer, about 6.1% of the pesticidal component eluted in 8 days after start of the test, after which the elution rapidly progressed until the total elution reached about 86% on the $42^{nd}$ day after the start. In the Referential Example using the existing BION Granule 2, total elution on the $7^{th}$ day was as high as about 6.2%, after which the elution rate increased relatively slowly.

TABLE 1

Elution rates (in %) of each example

| | Days elapsed | | | | | | | | | |
|---|---|---|---|---|---|---|---|---|---|---|
| | 0 | 7 | 14 | 21 | 28 | 35 | 42 | 49 | 56 | 112 |
| Example 1 | 0 | 3 | 14 | 36 | 42 | 53 | 58 | 59 | 63 | 85 |
| Example 2 | 0 | 3 | 14 | 37 | 48 | 56 | 58 | 62 | 63 | 88 |
| Referential Example | 0 | 6 | 14 | 20 | 28 | 33 | — | 41 | 50 | — |
| Comparative Example | 0 | 6 | 25 | 52 | 64 | 72 | 93 | — | — | — |

TEST EXAMPLE 2

Efficacy Test in Application to Rice Plants

Each of the aqueous suspensions containing the microcapsule of Example 1 and Comparative Example 2 was applied to seedling boxes filled with soil in the seeding period and greening period of rice plant, by means of a watering pot so that the quantity of applied microcapsule corresponded to 1% original pesticide per gram. As the rice plant, KOSHIHIKARI variety was used. After seeding and coverage with soil, the system was kept at +30° C. under a high humidity condition for 3 days. After the greening period of 1–2 days, namely about 30 days after the seeding, the seedlings were transplanted into pots as imaginary main fields. 45 days after the transplantation, the number of disease spots on the leaves (disease number) caused by Pyricularia oryzae (blast) was counted.

As control samples, plants having passed the same raising steps as above without any pesticidal treatment were used. As a referential example, a sample using BION Granule 2 was used. The BION Granule 2 was applied just before the transplantation to pots according to the existing registered method of application. Disease control value was calculated from the counted number of disease spots.

The results thus obtained are summarized in Table 2. The results of Table 2 demonstrates that the microcapsule of the present invention exhibits its efficacy in the same manner as the BION Granule 2 of referential example, which confirms that the microcapsule releases the active ingredient with an appropriate slow-releasing character.

TABLE 2

Disease control value of each example

| | | Blast after 45 days | |
|---|---|---|---|
| | Time of application | No. of disease spots* | Disease control value** |
| Control sample | — | 22.6 | |
| Referential Example | Just before Transplantation | 9.7 | |
| Comparative Example 2 | Upon seeding In Greening period | 15.6 14.3 | 31 37 |
| Example 1 | Upon seeding In greening period | 8.1 6.9 | 64 69 |

*Number of disease spots of blast on leaves in 25 seedlings.
**Disease control value (%): The result in control sample is taken as zero.

TEST EXAMPLE 3

Chemical Injury Test in Application to Rice Plants

Each of the aqueous suspensions containing the microcapsules prepared in Example 1 and Comparative Example 2 was applied to the seedling box by means of a watering pot so that the quantity of microcapsule applied corresponded to 1% original pesticide per gram, and the chemical injury was investigated. Controls using no pesticide and referential example using BION Granule 2 were also similarly tested, provided that the BION Granule 2 was applied just before transplantation. Seeding and raising of seedling were carried out in the same manner as in Test Example 2. In order to examine the chemical injury, the plant growth was visually observed and evaluated on the $14^{th}$, $25^{th}$ and $34^{th}$ day after the transplantation, taking the plant growth in the untreated plot (control) as 100%.

The results are summarized in Table 3.

TABLE 3

Plant growth after transplantation

| | | Plant growth (%) after transplantation | | |
|---|---|---|---|---|
| | Time of application | $14^{th}$ day | $25^{th}$ day | $34^{th}$ day |
| Control sample | — | 100 | 100 | 100 |
| Referential Example | Just before Transplantation | 100 | 90 | 95 |
| Comparative Example 2 | Upon seeding In Greening period | 95 100 | 85 85 | 90 80 |
| Example 1 | Upon seeding In greening period | 100 100 | 95 100 | 100 100 |

As a result, it has been revealed that, when using the microcapsule of Example 1, the degree of occurrence of chemical injury is so low, independently of the time of application thereof, namely at the time of seeding as well as in the greening period, that said occurrence is within the range of tolerance at practical application. The microcapsule of Example 1 exhibits efficacy against rice blast as high as that of BION Granule 2, thereby confirming the desired and appropriate slow-release property.

As has been described above, the present invention provides a microcapsule containing a solid pesticide, the release of the pesticide from which can be sufficiently controlled.

Since the microcapsule of the present invention retains the slow-release character thereof over a long period of time, the development of chemical injury can be avoided especially in the infant period of plants, and the wasteful loss of expensive pesticide caused by its elution before the period in which the efficacy is desired can be suppressed. Further, the present invention makes it possible to use a combination of a plurality of pesticides which otherwise have so far not been not combinable, i.e. have to be separately applied, or to form such pesticides into a single composition which with the separate encapsulation of the active pesticides avoids decomposition of the chemical agents. As above, the microcapsule of the present invention greatly improves the workability of pesticide application and thereby contributes to saving of labor. Further, the microcapsule is relatively safe to human body even if it enters the human body accidentally. Further, the microcapsule of the present invention makes it possible to relax the existing control system of poisonous and powerful agents.

According to the method for producing microcapsule of the present invention, solid pesticides which have so far been difficult to encapsulate can be formed into a microcapsule having a slow-releasing character without forming any beads due to self-agglomeration of resin prepolymer.

What is claimed is:

1. A microcapsule comprising a solid pesticide as a core material, which is coated with a wall material, which wall material is a resin formed by subjecting a sparingly water-soluble melamine-formaldehyde resin prepolymer to a polycondensation reaction in the presence of a dispersant, which dispersant is a condensation product of naphthaienesulfonic acid and/or alkylnaphthalenesulfonic acid and formaldehyde or a salt of said condensation product, characterised in that the solubility of water in said sparingly water-soluble melamine-formaldehyde resin prepolymer is 2000 g or less of water per 100 g of the solid component of the prepolymer at +25° C.

2. A microcapsule according to claim 1, wherein said dispersant is a sodium naphthalenesulfonate-formaldehyde condensation product having a weight-average molecular weight of 500 to 8000.

3. A microcapsule according to claim 1, wherein said solid pesticide is a pesticide having a melting point of +20° C. or above.

4. A microcapsule according to claim 1, which is used in the raising of rice plants.

5. A microcapsule according to claim 3, wherein said solid pesticide is acibenzolar-S-methyl.

6. A microcapsule according to claim 3, wherein said solid pesticide is thiamethoxam.

7. A method for producing a microcapsule as claimed in claim 1, comprising a step of dissolving, in water, a dispersant which dispersant is a condensation product of naphthalenesulfonic acid and/or alkylnaphthalenesulfonic acid and formaldehyde or a salt of said condensation product, a step of adding a sparingly water-soluble melamine-formaldehyde resin prepolymer to the solution obtained above while stirring the solution, characterised in that the solubility of water in said sparingly water-soluble melamine-formaldehyde resin prepolymer is 2000 g or less of water per 100 g of the solid component of the prepolymer at +25° C., a step of adding a solid pesticide, and a step of carrying out a polycondensation of the prepolymer under an acidic condition.

8. A method according to claim 7, wherein said solid pesticide is used in an amount of from 1 to 50% by weight, said dispersant is used in an amount of from 1 to 20% by weight and said sparingly water-soluble melamine-formaldehyde resin prepolymer is used in an amount of from 1 to 60% by weight, based on the total weight of the liquid mixture subject to the polycondensation reaction.

9. A method according to claim 7, wherein said dispersant is a sodium naphthalenesulfonate-formaldehyde condensation product having a weight-average molecular weight of 500 to 8000.

10. A method according to claim 7, wherein said solid pesticide is a pesticide having a melting point of +20° C. or above.

11. A method according to claim 7, wherein said microcapsule is a microcapsule for use in the raising of rice plants.

12. A method according to claim 10, wherein said solid pesticide is acibenzolar-S-methyl.

13. A method according to claim 10, wherein said solid pesticide is thiamethoxam.

14. A microcapsule characterized by being produced by the method according to claim 7.

15. A microcapsule according to claim 1, wherein the release of the pesticide component is started by contact with water, the weight of which water is at least 100 times as large as that of the microcapsule.

16. An aqueous suspension composition containing the microcapsule according to claim 1, in an amount of 2% by weight or more.

17. A method for application of a microcapsule comprising scattering a microcapsule according to claim 1, to the soil on which a plant is raised.

18. A method for application of a microcapsule comprising scattering a microcapsule according to claim 15 to the soil on which a plant is raised.

19. A method for the application of a microcapsule comprising scattering a microcapsule according to claim 1 to the soil on which a plant is raised, at the time of sowing plant seeds or during the growing period of the plant.

20. A method for the application of a microcapsule comprising scattering a microcapsule according to claim 15 to the soil on which a plant is raised, at the time of sowing plant seeds or during the growing period of the plant.

21. A method for the application of a microcapsule comprising scattering the microcapsule according to claim 1 in the period from the time of sowing a rice seed to the time of transplanting a rice plant to a main paddy field.

22. A method for the application of a microcapsule comprising scattering the microcapsule according to claim 6 in the period from the time of sowing a rice seed to the time of transplanting a rice plant to a main paddy field.

23. A method for the application of a microcapsule comprising scattering a microcapsule according to claim 1 directly to a main paddy field after transplantation of rice seedlings into the main paddy field.

24. A method for the application of a microcapsule comprising scattering a microcapsule according to claim 6 directly to a main paddy field after transplantation of rice seedlings into the main paddy field.

* * * * *